United States Patent
Thomas et al.

(10) Patent No.: US 11,643,402 B2
(45) Date of Patent: *May 9, 2023

(54) GAS PHASE METHODS TO DECARBOXYLATE CANNABINOIDS

(71) Applicant: Natural Extraction Systems, LLC, Boulder, CO (US)

(72) Inventors: C. Russell Thomas, Boulder, CO (US); Matthew M. DePalo, Wheat Ridge, CO (US)

(73) Assignee: NATURAL EXTRACTION SYSTEMS, LLC, Boulder, CO (US)

( * ) Notice: Subject to any disclaimer, the term of this patent is extended or adjusted under 35 U.S.C. 154(b) by 83 days.

This patent is subject to a terminal disclaimer.

(21) Appl. No.: 16/889,428

(22) Filed: Jun. 1, 2020

(65) Prior Publication Data

US 2020/0290988 A1 Sep. 17, 2020

Related U.S. Application Data

(63) Continuation of application No. 16/271,782, filed on Feb. 9, 2019, now Pat. No. 10,669,248.

(60) Provisional application No. 62/803,408, filed on Feb. 8, 2019, provisional application No. 62/717,235, filed on Aug. 10, 2018.

(51) Int. Cl.
| | |
|---|---|
| *C07D 311/78* | (2006.01) |
| *C07C 29/80* | (2006.01) |
| *C07C 67/08* | (2006.01) |
| *B01D 5/00* | (2006.01) |

(52) U.S. Cl.
CPC ............ *C07D 311/78* (2013.01); *C07C 29/80* (2013.01); *C07C 67/08* (2013.01); *B01D 5/006* (2013.01)

(58) Field of Classification Search
CPC ....... C07D 311/78; C07C 29/80; C07C 67/08; C07C 67/01; B01D 5/006
See application file for complete search history.

(56) References Cited

U.S. PATENT DOCUMENTS

| | | |
|---|---|---|
| 2,467,435 A | 4/1949 | Langhurst |
| 2,805,981 A | 9/1957 | Cavin |
| 3,270,437 A | 9/1966 | Lara |
| 4,227,997 A | 10/1980 | Shaddock |
| 4,279,824 A | 7/1981 | McKinney |
| 4,396,487 A | 8/1983 | Strumskis |
| 4,752,307 A | 6/1988 | Asmus |
| 5,002,784 A | 3/1991 | Paré |
| 5,026,549 A | 6/1991 | Coutiere |
| 5,235,992 A | 8/1993 | Sensabaugh, Jr. |
| 5,408,924 A | 4/1995 | Arendt |
| 5,458,897 A | 10/1995 | Paré |
| 6,019,819 A | 2/2000 | Williams |
| 6,248,910 B1 | 6/2001 | Franke |
| 6,403,126 B1 | 6/2002 | Webster |
| 6,860,998 B1 | 3/2005 | Wilde |
| 7,001,502 B1 | 2/2006 | Satchwell |
| 7,001,629 B1 | 2/2006 | Mengal |
| 7,344,736 B2 | 3/2008 | Whittle |
| 7,622,140 B2 | 11/2009 | Whittle |
| 7,833,298 B2 | 11/2010 | Larnholm |
| 8,062,410 B2 | 11/2011 | Bullinger |
| 8,329,229 B2 | 12/2012 | Gonzalez |
| 8,343,553 B2 | 1/2013 | Hospodor |
| 8,445,034 B1 | 5/2013 | Coles, Jr. |
| 9,038,413 B2 | 5/2015 | Howard |
| 9,987,567 B1 | 6/2018 | Ko |
| 10,159,908 B2 | 12/2018 | Thomas |
| 10,195,159 B2 | 2/2019 | Whittle |
| 10,238,705 B2 | 3/2019 | Speier |
| 10,456,708 B2 | 10/2019 | Thomas |
| 10,617,974 B2 | 4/2020 | Thomas |
| 10,669,248 B2 | 6/2020 | Thomas |
| 10,822,320 B2 | 11/2020 | Thomas |
| 11,021,674 B2 | 6/2021 | Thomas |
| 2002/0139097 A1 | 10/2002 | Brilmaker |
| 2004/0049059 A1 | 3/2004 | Mueller |
| 2004/0147767 A1 | 7/2004 | Whittle |
| 2004/0147769 A1 | 7/2004 | Davis |
| 2004/0187340 A1 | 8/2004 | Chemat et al. |
| 2005/0042172 A1 | 2/2005 | Whittle |
| 2005/0172802 A1 | 8/2005 | Betting |
| 2009/0054711 A1 | 2/2009 | Lawrence |
| 2010/0119606 A1 | 5/2010 | Whittle |
| 2011/0133120 A1 | 6/2011 | McGhee |
| 2012/0012002 A1 | 1/2012 | Kaneko |
| 2012/0157719 A1 | 6/2012 | Teles |
| 2013/0240347 A1 | 9/2013 | Hackleman |
| 2014/0001027 A1 | 1/2014 | Balass |
| 2014/0113010 A1 | 4/2014 | Hospodor |

(Continued)

FOREIGN PATENT DOCUMENTS

| | | |
|---|---|---|
| CA | 2472561 A1 | 8/2002 |
| CN | 201643760 U | 11/2010 |

(Continued)

OTHER PUBLICATIONS

WANG. Cannabis and Cannabinoid Research, 2016, 1.1, 262-271 (Year: 2016).*
Kanter et al., "Qualitative determination of delta9-tetrahydrocannabinol and delta9-tetrahydrocannabinolic acid in marihuana by high-pressure liquid chromatograph," Journal of Chromatography, 1979, pp. 504-508, vol. 171.
Veress et al., "Determination of cannabinoid acids by high-performance liquid chromatography of their neutral derivatives formed by thermal decarboxylation: I. Study of the decarboxylation process in open reactors," Journal of Chromatography, 1990, pp. 339-347, vol. 520.
Benmoussa, H. et al. Enhanced solvent-free microwave extraction of Foeniculum vulgare Mill. essential oil seeds using double walled reactor. Arabian Journal of Chemistry (2019) 12, 3863-3870.

(Continued)

*Primary Examiner* — Noble E Jarrell
(74) *Attorney, Agent, or Firm* — Holland & Hart LLP

(57) ABSTRACT

Various aspects of this disclosure relate to gas phase methods to decarboxylate cannabinoid carboxylic acids.

20 Claims, 1 Drawing Sheet

(56) References Cited

U.S. PATENT DOCUMENTS

| | | |
|---|---|---|
| 2014/0193303 A1 | 7/2014 | Ellis |
| 2014/0271940 A1 | 9/2014 | Wurzer et al. |
| 2015/0068113 A1 | 3/2015 | Conner |
| 2015/0252286 A1 | 9/2015 | Scialdone |
| 2016/0038437 A1 | 2/2016 | Whittle |
| 2016/0053199 A1 | 2/2016 | Clodoveo |
| 2018/0000857 A1 | 1/2018 | Kotra et al. |
| 2018/0078874 A1 | 3/2018 | Thomas |
| 2018/0296617 A1 | 10/2018 | Rivas |

FOREIGN PATENT DOCUMENTS

| | | |
|---|---|---|
| CN | 101553702 B | 6/2012 |
| CN | 105943615 A | 9/2016 |
| EP | 2644039 A1 | 10/2013 |
| EP | 3453397 A1 | 3/2019 |
| FR | 2742358 A1 | 6/1997 |
| GB | 635121 | 4/1950 |
| GB | 2372714 A | 9/2002 |
| JP | 4388715 B2 | 11/2002 |
| JP | 4849578 B1 | 1/2012 |
| WO | 2002089945 A2 | 11/2002 |
| WO | 2014000077 A1 | 1/2014 |
| WO | 2015049585 A2 | 4/2015 |
| WO | 2016153347 A1 | 9/2016 |
| WO | 2016161420 A1 | 10/2016 |
| WO | 2018009514 A1 | 1/2018 |

OTHER PUBLICATIONS

Filly, A. et al., Solvent-free microwave extraction of essential oil from aromatic herbs: From laboratory pilot industrial scale. Food Chemistry 150(2014); 193-198.

Petrov, V.M. et al. Microwave Absorbing Materials. Inorganic Materials vol. 37, No. 2, 2001, pp. 93-98.

Wang, Z. et al. Improved solvent-free microwave extraction of essential oil from dried Cuminum cyminum L. and Zanthoxylum bungeanum Maxim. Journal of Chromatography A, 1102 (2006) 11-17.

* cited by examiner

GAS PHASE METHODS TO DECARBOXYLATE CANNABINOIDS

CROSS-REFERENCE TO RELATED APPLICATIONS

This patent application is a continuation of prior U.S. patent application Ser. No. 16/271,782, filed Feb. 9, 2019, which granted as U.S. Pat. No. 10,669,248, which claims priority to U.S. Provisional Patent Application No. 62/717,235, filed Aug. 10, 2018, and U.S. Provisional Patent Application No. 62/803,408, filed Feb. 8, 2019, and each of the three applications is incorporated by reference in its entirety.

BACKGROUND

Industrial hemp and other forms of cannabis contain a variety of different cannabinoids, which predominantly each contain a carboxyl group. The production of therapeutic pharmaceuticals and psychoactive drugs from cannabis generally utilizes a decarboxylation step, which typically involves prolonged heating. Such heating also generally produces undesirable chemical modifications. Improved methods to decarboxylate cannabinoids are desirable.

SUMMARY

Various aspects of this patent document relate to a method to chemically-modify a cannabinoid molecule, comprising: (a) providing a composition comprising cannabinoids, wherein the composition has a surface-area-to-volume area that is greater than 1000 per meter; the cannabinoids comprise a native cannabinoid molecule; the native cannabinoid molecule comprises a carboxyl group; and the native cannabinoid molecule is in either a liquid phase or a solid phase; (b) contacting the composition with sufficient energy to convert the native cannabinoid molecule into (i) a carbon dioxide molecule and (ii) a modified cannabinoid molecule in a gas phase; (c) contacting the modified cannabinoid molecule with a heat sink to condense the modified cannabinoid molecule into a condensed cannabinoid molecule in a liquid distillate; and (d) collecting the liquid distillate.

In some embodiments, the composition comprises a particle; the particle comprises the native cannabinoid molecule; the method comprises suspending the particle in the gas phase; and the method comprises contacting the composition with the sufficient energy while the particle is suspended in the gas phase.

In some embodiments, the composition comprises a droplet; the droplet comprises the native cannabinoid molecule; the method comprises suspending the droplet in the gas phase; and the method comprises contacting the composition with the sufficient energy while the droplet is suspended in the gas phase.

In some embodiments, contacting the composition with the sufficient energy comprises contacting the composition with less than 100 kilojoules of energy per gram of the composition.

In some embodiments, contacting the composition with the sufficient energy comprises contacting the composition with at least 1 kilowatt of power per gram of the composition and no greater than 100 kilowatts of power per gram of the composition for at least 200 milliseconds and no greater than 20 seconds.

In some embodiments, contacting the composition with the sufficient energy comprises irradiating the composition.

In some embodiments, contacting the composition with the sufficient energy comprises convectively heating the composition.

In some embodiments, contacting the composition with the sufficient energy comprises conductively heating the composition.

In some embodiments, the method further comprises directing the composition along a path having a length of at least 4 meters at a rate of at least 2 meters per second. In some specific embodiments, the path comprises one or more surfaces, and the method comprises heating the one or more surfaces to a temperature of at least 190 degrees Celsius and no greater than 250 degrees Celsius.

In some embodiments, composition comprises a non-volatile molecule; the method comprises separating the modified cannabinoid molecule from the non-volatile molecule; the separating is performed after converting the native cannabinoid molecule into (i) the carbon dioxide molecule and (ii) the modified cannabinoid molecule in the gas phase; and the separating is performed prior to contacting the modified cannabinoid molecule with the heat sink. In some specific embodiments, non-volatile molecule is either chlorophyll, cellulose, a nucleic acid, a protein, a carbohydrate, a sugar, a triglyceride, or a phospholipid.

In some embodiments, the method comprises contacting the modified cannabinoid molecule with the heat sink less than 240 seconds after contacting the composition with the sufficient energy.

In some embodiments, the liquid distillate comprises one or both of cannabidiol and tetrahydrocannabinol at a combined concentration of greater than 6 percent by weight; and the liquid distillate comprises cannabinol at a concentration of less than 0.8 percent by weight.

In some embodiments, the liquid distillate comprises each of cannabidiol, tetrahydrocannabinol, and cannabigerol.

In some embodiments, the liquid distillate comprises ethanol at a concentration of at least 50 percent by weight.

In some embodiments, the liquid distillate comprises a non-cannabinoid molecule and the condensed cannabinoid molecule; and the method comprises separating the non-cannabinoid molecule from the condensed cannabinoid molecule to produce a product comprising the condensed cannabinoid molecule at a concentration of at least 55 percent by weight.

In some embodiments, the native cannabinoid molecule is cannabigerolic acid; the modified cannabinoid molecule is cannabigerol; and the condensed cannabinoid molecule is cannabigerol.

Various aspects of this patent document relate to a method to chemically-modify a cannabinoid molecule, comprising: (a) providing a composition comprising cannabinoids, wherein the composition has a surface-area-to-volume area that is greater than 1000 per meter; the cannabinoids comprise a native cannabinoid molecule; the native cannabinoid molecule comprises a carboxyl group; the native cannabinoid molecule is in either a liquid phase or a solid phase; the composition comprises a particle; the particle comprises the native cannabinoid molecule; and the composition comprises a non-volatile molecule; (b) suspending the particle in a gas phase; (c) contacting the composition with sufficient energy to convert the native cannabinoid molecule into (i) a carbon dioxide molecule and (ii) a modified cannabinoid molecule in the gas phase while the particle is suspended in the gas phase, wherein the sufficient energy is less than 100 kilojoules of energy per gram of the composition; (d) separating the modified cannabinoid molecule from the non-volatile molecule; (e) contacting the modified cannabinoid molecule with a heat sink to condense the modified cannabinoid molecule into a condensed cannabinoid molecule in a liquid distillate; (f) collecting the liquid distillate, wherein the liquid distillate comprises the condensed cannabinoid molecule and a non-cannabinoid molecule; and (g) separating the non-cannabinoid molecule from the condensed cannabinoid molecule to produce a product comprising the condensed cannabinoid molecule at a concentration of at least 55 percent by weight.

Various aspects of this patent document relate to a method to chemically-modify a cannabinoid molecule, comprising: (a) providing a composition comprising cannabinoids, wherein the composition has a surface-area-to-volume area that is greater than 1000 per meter; the cannabinoids comprise a native cannabinoid molecule; the native cannabinoid molecule comprises a carboxyl group; the native cannabinoid molecule is cannabigerolic acid; the native cannabinoid molecule is in either a liquid phase or a solid phase; the composition comprises a particle; the particle comprises the native cannabinoid molecule; and the composition comprises a non-volatile molecule; (b) suspending the particle in a gas phase; (c) contacting the composition with sufficient energy to convert the native cannabinoid molecule into (i) a carbon dioxide molecule and (ii) a modified cannabinoid molecule in the gas phase while the particle is suspended in the gas phase, wherein the sufficient energy is less than 100 kilojoules of energy per gram of the composition, and the modified cannabinoid molecule is cannabigerol; (d) separating the modified cannabinoid molecule from the non-volatile molecule; (e) contacting the modified cannabinoid molecule with a heat sink to condense the modified cannabinoid molecule into a condensed cannabinoid molecule in a liquid distillate, wherein the condensed cannabinoid molecule is cannabigerol; (f) collecting the liquid distillate, wherein the liquid distillate comprises the condensed cannabinoid molecule and a non-cannabinoid molecule; and (g) separating the non-cannabinoid molecule from the condensed cannabinoid molecule to produce a product comprising the condensed cannabinoid molecule at a concentration of at least 55 percent by weight.

DETAILED DESCRIPTION

Figure 1:
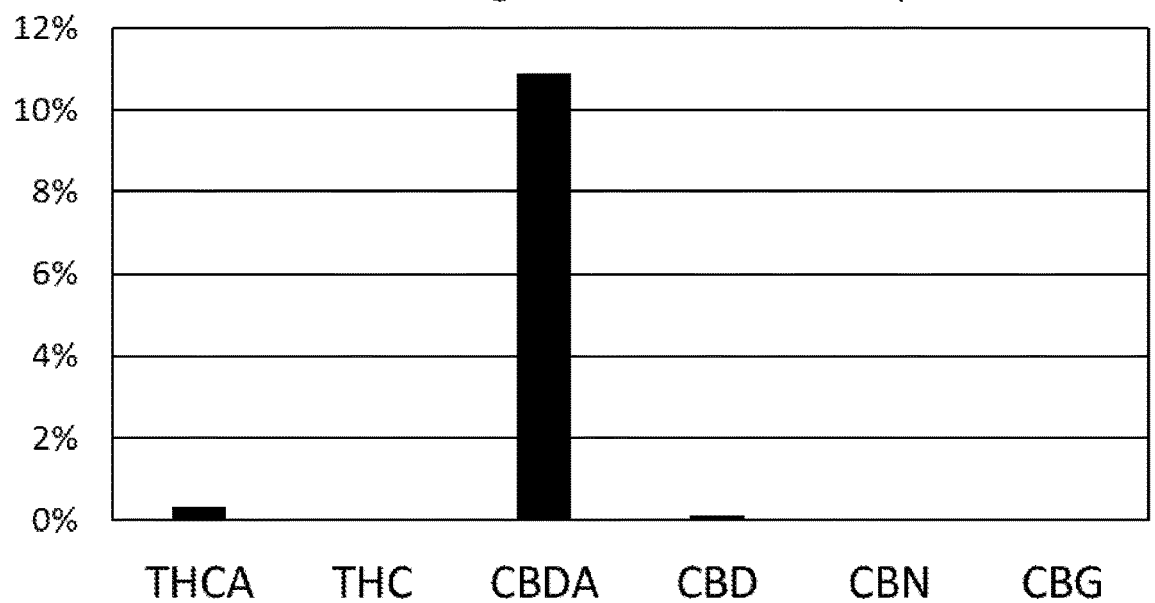
FIG. 1 is a bar graph depicting the THCA, THC, CBDA, CBD, CBN, and CBG concentrations found in a typical sample of USDA organic industrial hemp.

Various aspects of the disclosure relate to a method to chemically modify a cannabinoid molecule. In some embodiments, a chemical modification is a decarboxylation of a cannabinoid carboxylic acid. In some specific embodiments, a chemical modification is the conversion of cannabidiolic acid ("CBDA") or cannabidiolate into cannabidiol ("CBD"). In some specific embodiments, a chemical modification is the conversion of cannabidivarin carboxylic acid ("CBDVA") or the conjugate base of CBDVA into cannabidivarin ("CBDV"). In some specific embodiments, a chemical modification is the conversion of tetrahydrocannabinolic acid ("THCA") or tetrahydrocannabinolate into tetrahydrocannabinol ("THC"). In some specific embodiments, a chemical modification is the conversion of tetrahydrocannabivarin carboxylic acid ("THCVA") or tetrahydrocannabivarin carboxylate into tetrahydrocannabivarin ("THCV"). In some specific embodiments, a chemical modification is the conversion of perrottetinenic acid or the conjugate base of perrottetinenic acid into perrottetinene.

In some embodiments, a method comprises providing a composition comprising cannabinoids, in which the cannabinoids comprise a native cannabinoid molecule, the native cannabinoid molecule comprises a carboxyl group, and the native cannabinoid molecule is in a liquid phase or a solid phase in the composition.

In some embodiments, a method comprises contacting a composition with sufficient energy to convert a native cannabinoid molecule of the composition into (i) a carbon dioxide molecule and (ii) a modified cannabinoid molecule in a gas phase.

In some embodiments, a method comprises contacting a modified cannabinoid molecule with a heat sink to condense the modified cannabinoid molecule into a condensed cannabinoid molecule in a liquid distillate.

In some embodiments, a method comprises collecting a liquid distillate.

In some embodiments, a composition comprises a plant material. In some very specific embodiments, a composition comprises a plant material, and the plant material comprises a native cannabinoid molecule. In some specific embodiments, a composition comprises a ground plant material. In some embodiments, a composition has a surface-area-to-volume ratio greater than 1000 per meter.

In some embodiments, a plant material is a species of the genus *Cannabis*. In some specific embodiments, a plant material is *Cannabis sativa*. In some specific embodiments, a plant material is *Cannabis indica*. In some specific embodiments, a plant material is *Cannabis ruderalis*. In some very specific embodiments, a plant material is *Cannabis sativa* forma indica. In some specific embodiments, a plant material lacks THC and potential THC at a combined concentration by weight exceeding 0.3%. The term "potential THC" refers to THCA multiplied by 314.47 (the molecular weight of THC) and divided by 358.48 (the molecular weight of THCA). A plant material that lacks THC and contains 0.33% THCA, for example, contains THC and potential THCA at a combined concentration by weight of 0.29%.

In some embodiments, a composition comprises an extracted oil from the genus *Cannabis*. In some specific embodiments, a composition comprises an extracted oil from industrial hemp.

In some embodiments, a composition comprises marijuana or a composition is derived from marijuana.

In some embodiments, a composition is a liquid such as an oil. In some embodiments, a composition is an aerosol. In some specific embodiments, a composition comprises a suspension of solid particles in a gas. In some specific embodiments, a composition comprises a suspension of liquid droplets in a gas. In some specific embodiments, a composition comprises a powder. In some specific embodiments, a composition comprises crystals. In some specific embodiments, a composition comprises wax.

In some embodiments, a composition is suspended in a gas phase.

In some embodiments, a method comprises grinding plant material. In some embodiments, a method comprises separating particles of industrial hemp, marijuana, or other plant material by size such as by using a screen, mesh, or particle classifier.

In some embodiments, a native cannabinoid molecule is selected from one or more of THCA, THCVA, tetrahydrocannabiorcolic acid ("THCOA"), CBDA, CBDVA, cannabidiorcolic acid ("CBDOA"), cannabichromenic acid ("CBCA"), cannabichromevarinic acid ("CBCVA"), cannabigerolic acid ("CBGA"), cannabigerovarinic acid ("CBGVA"), cannabicyclolic acid ("CBLA"), cannabielsoic acid ("CBEA"), perrottetinenic acid, carboxylates of any of the preceding molecules, naturally-occurring ethers of any of the preceding molecules, and stereoisomers of any of the preceding molecules.

In some embodiments, a modified cannabinoid molecule or condensed cannabinoid molecule is selected from one or more of THC, THCV, tetrahydrocannabiorcol ("THCO"), CBD, CBDV, cannabidiorcol, ("CBDO"), cannabichromene ("CBC"), cannabichromevarin ("CBCV"), cannabigerol ("CBG"), cannabigerovarin ("CBGV"), cannabicyclol ("CBL"), cannabielsoin ("CBE"), perrottetinene, naturally-occurring ethers of any of the preceding molecules, and stereoisomers of any of the preceding molecules.

In some very specific embodiments, a native cannabinoid molecule is CBDA, which is also known as 2,4-dihydroxy-3-[(1R,6R)-6-isopropenyl-3-methylcyclohex-2-en-1-yl]-6-pentylbenzoic acid.

In some very specific embodiments, a native cannabinoid molecule is CBDVA, which is also known as 2,4-dihydroxy-3-[(1R,6R)-6-isopropenyl-3-methylcyclohex-2-en-1-yl]-6-propylbenzoic acid.

In some very specific embodiments, a native cannabinoid molecule is THCA, which is also known as (6aR,10aR)-1-hydroxy-6,6,9-trimethyl-3-pentyl-6a,7,8,10a-tetrahydro-6H-benzo[c]chromene-2-carboxylic acid.

In some very specific embodiments, a native cannabinoid molecule is THCVA, which is also known as (6aR,10aR)-1-hydroxy-6,6,9-trimethyl-3-propyl-6a,7,8,10a-tetrahydro-6H-benzo[c]chromene-2-carboxylic acid.

In some very specific embodiments, a native cannabinoid molecule is perrottetinenic acid, which is also known as (6aS,10aR)-1-hydroxy-6,6,9-trimethyl-3-(2-phenylethyl)-6a,7,8,10a-tetrahydro-6H-benzo[c]chromene-2-carboxylic acid.

In some specific embodiments, a modified cannabinoid molecule or condensed cannabinoid molecule is CBD, which is also known as 2-[(1R,6R)-6-isopropenyl-3-methylcyclohex-2-en-1-yl]-5-pentylbenzene-1,3-diol. In some very specific embodiments, a modified cannabinoid molecule is CBD. In some very specific embodiments, a condensed cannabinoid molecule is CBD.

In some specific embodiments, a modified cannabinoid molecule or condensed cannabinoid molecule is CBDV, which is also known as 2-[(1R,6R)-6-isopropenyl-3-methylcyclohex-2-en-1-yl]-5-propylbenzene-1,3-diol. In some very specific embodiments, a modified cannabinoid molecule is CBDV. In some very specific embodiments, a condensed cannabinoid molecule is CBDV.

In some specific embodiments, a modified cannabinoid molecule or condensed cannabinoid molecule is THC, which is also known as (6aR,10aR)-6,6,9-trimethyl-3-pentyl-6a,7,8,10a-tetrahydro-6H-benzo[c]chromen-1-ol. In some very specific embodiments, a modified cannabinoid molecule is THC. In some very specific embodiments, a condensed cannabinoid molecule is THC.

In some specific embodiments, a modified cannabinoid molecule or condensed cannabinoid molecule is THCV, which is also known as (6aR,10aR)-6,6,9-trimethyl-3-propyl-6a,7,8,10a-tetrahydro-6H-benzo[c]chromen-1-ol. In some very specific embodiments, a modified cannabinoid molecule is THCV. In some very specific embodiments, a condensed cannabinoid molecule is THCV.

In some specific embodiments, a modified cannabinoid molecule or condensed cannabinoid molecule is perrottetinene, which is also known as (6aS,10aR)-6,6,9-trimethyl-3-(2-phenylethyl)-6a,7,8,10a-tetrahydro-6H-benzo[c]chromen-1-ol. In some very specific embodiments, a modified cannabinoid molecule is perrottetinene. In some very specific embodiments, a condensed cannabinoid molecule is perrottetinene.

In some specific embodiments, a native cannabinoid molecule is THCA, a modified cannabinoid molecule is THC, and a condensed cannabinoid molecule is THC.

In some specific embodiments, a native cannabinoid molecule is THCVA, a modified cannabinoid molecule is THCV, and a condensed cannabinoid molecule is THCV.

In some specific embodiments, a native cannabinoid molecule is THCOA, a modified cannabinoid molecule is THCO, and a condensed cannabinoid molecule is THCO.

In some specific embodiments, a native cannabinoid molecule is CBDA, a modified cannabinoid molecule is CBD, and a condensed cannabinoid molecule is CBD.

In some specific embodiments, a native cannabinoid molecule is CBDVA, a modified cannabinoid molecule is CBDV, and a condensed cannabinoid molecule is CBDV.

In some specific embodiments, a native cannabinoid molecule is CBDOA, a modified cannabinoid molecule is CBDO, and a condensed cannabinoid molecule is CBDO.

In some specific embodiments, a native cannabinoid molecule is CBCA, a modified cannabinoid molecule is CBC, and a condensed cannabinoid molecule is CBC.

In some specific embodiments, a native cannabinoid molecule is CBCVA, a modified cannabinoid molecule is CBCV, and a condensed cannabinoid molecule is CBCV.

In some specific embodiments, a native cannabinoid molecule is CBGA, a modified cannabinoid molecule is CBG, and a condensed cannabinoid molecule is CBG.

In some specific embodiments, a native cannabinoid molecule is CBGVA, a modified cannabinoid molecule is CBGV, and a condensed cannabinoid molecule is CBGV.

In some specific embodiments, a native cannabinoid molecule is CBLA, a modified cannabinoid molecule is CBL, and a condensed cannabinoid molecule is CBL.

In some specific embodiments, a native cannabinoid molecule is CBEA, a modified cannabinoid molecule is CBE, and a condensed cannabinoid molecule is CBE.

In some specific embodiments, a native cannabinoid molecule is perrottetinenic acid, a modified cannabinoid molecule is perrottetinene, and a condensed cannabinoid molecule is perrottetinene.

In some embodiments, a composition comprises a plurality of cannabinoids, and at least 95% of the cannabinoids of the plurality of cannabinoids comprises a carboxyl group.

In some embodiments, a composition comprises a native cannabinoid molecule at a concentration of at least 5% by weight. In some embodiments, a composition comprises a native cannabinoid molecule at a concentration by weight of 1% to 10%, 5% to 15%, 10% to 20%, 15% to 25%, 20% to 30%, or 25% to 35%. In some specific embodiments, a composition comprises CBDA, CBDVA, THCA, THCVA, and CBGA at a concentration of at least 5% by weight. In some specific embodiments, a composition comprises CBDA, CBDVA, THCA, THCVA, and CBGA at a concentration by weight of 1% to 10%, 5% to 15%, 10% to 20%, 15% to 25%, 20% to 30%, or 25% to 35%. In some very specific embodiments, a composition comprises CBDA at a concentration of at least 5% by weight. In some very specific embodiments, a composition comprises CBDA at a concentration by weight of 1% to 10%, 5% to 15%, 10% to 20%, 15% to 25%, 20% to 30%, or 25% to 35%. In some very specific embodiments, a composition comprises CBDVA at a concentration of at least 0.1% by weight. In some very specific embodiments, a composition comprises CBDVA at a concentration by weight of 0.1% to 10%, 5% to 15%, 10% to 20%, 15% to 25%, 20% to 30%, or 25% to 35%. In some very specific embodiments, a composition comprises THCA at a concentration of at least 20% by weight. In some very specific embodiments, a composition comprises THCA at a concentration by weight of 10% to 20%, 15% to 25%, 20% to 30%, or 25% to 35%. In some very specific embodiments, a composition comprises THCVA at a concentration of at least 1% by weight. In some very specific embodiments, a composition comprises THCVA at a concentration by weight of 0.1% to 10%, 5% to 15%, 10% to 20%, 15% to 25%, 20% to 30%, or 25% to 35%.

In some embodiments, a method comprises suspending a particle of a composition comprising cannabinoids in a gas phase, in which the particle comprises a native cannabinoid molecule. In some specific embodiments, a composition comprising a native cannabinoid molecule is contacted with sufficient energy to convert the native cannabinoid molecule into (i) a carbon dioxide molecule and (ii) a modified cannabinoid molecule in a gas phase while a particle of the composition comprising the native cannabinoid molecule is suspended in the gas phase.

In some embodiments, a method comprises suspending a plurality of particles of a composition comprising cannabinoids in a gas phase, in which the plurality of particles comprises a native cannabinoid molecule. In some specific embodiments, a composition comprising a native cannabinoid molecule is contacted with sufficient energy to convert the native cannabinoid molecule into (i) a carbon dioxide molecule and (ii) a modified cannabinoid molecule in a gas phase while a plurality of particles of the composition comprising the native cannabinoid molecule is suspended in the gas phase.

In some embodiments, a method comprises suspending a droplet of a composition comprising cannabinoids in a gas phase, in which the droplet comprises a native cannabinoid molecule. In some specific embodiments, a composition comprising a native cannabinoid molecule is contacted with sufficient energy to convert the native cannabinoid molecule into (i) a carbon dioxide molecule and (ii) a modified cannabinoid molecule in a gas phase while a droplet of the composition comprising the native cannabinoid molecule is suspended in the gas phase.

In some embodiments, a method comprises suspending a plurality of droplets of a composition comprising cannabinoids in a gas phase, in which the plurality of droplets comprises a native cannabinoid molecule. In some specific embodiments, a composition comprising a native cannabinoid molecule is contacted with sufficient energy to convert the native cannabinoid molecule into (i) a carbon dioxide molecule and (ii) a modified cannabinoid molecule in a gas phase while a plurality of droplets of the composition comprising the native cannabinoid molecule is suspended in the gas phase.

In some embodiments, a gas phase comprises water vapor at a concentration of at least 5% by volume. In some embodiments, a gas phase comprises ethanol vapor at a concentration of at least 5% by volume. In some embodiments, a gas phase comprises molecular nitrogen, ethanol vapor, water vapor, carbon dioxide, noble gases, cannabinoids, terpenes, terpene alcohols, and terpenoids at a total concentration of at least 90% by volume. In some specific embodiments, a gas phase comprises molecular nitrogen, ethanol vapor, water vapor, carbon dioxide, noble gases, cannabinoids, terpenes, terpene alcohols, and terpenoids at a total concentration of at least 95% by volume.

In some embodiments, contacting a composition with sufficient energy to convert a native cannabinoid molecule into (i) a carbon dioxide molecule and (ii) a modified cannabinoid molecule in a gas phase comprises contacting the composition with less than 100 kilojoules ("kJ") of energy per gram of the composition. In some specific embodiments, contacting a composition with sufficient energy to convert a native cannabinoid molecule into (i) a carbon dioxide molecule and (ii) a modified cannabinoid molecule in a gas phase comprises contacting the composition with 2 kJ to 50 kJ per gram of the composition.

In some embodiments, contacting a composition with sufficient energy to convert a native cannabinoid molecule into (i) a carbon dioxide molecule and (ii) a modified cannabinoid molecule in a gas phase comprises contacting the composition with energy at a rate of less than 100 kilowatts ("kW") of power per gram of the composition for a duration of less than 60 seconds. In some specific embodiments, contacting a composition with sufficient energy to convert a native cannabinoid molecule into (i) a carbon dioxide molecule and (ii) a modified cannabinoid molecule in a gas phase comprises contacting the composition with 1 kW to 100 kW of power per gram of the composition for 200 milliseconds to 20 seconds.

In some embodiments, a method comprises irradiating a composition, convectively heating a composition, or conductively heating a composition, in which contacting a composition with sufficient energy comprises one or more of irradiating the composition, convectively heating the composition, or conductively heating the composition. Suitable methods of irradiating a composition are described, for example, in PCT Patent Application Publication No. WO 2018/102711 A1, which is incorporated by reference in its entirety. Suitable methods of convectively heating a composition are described, for example, in PCT Patent Application Publication No. WO 2015/049585 A2, which is incorporated by reference in its entirety. Suitable methods of conductively heating a composition are described, for example, in PCT Patent Application Publication No. WO 2016/161420 A1 and WO 2017/192527 A1, each of which is incorporated by reference in its entirety.

In some embodiments, a method comprises contacting a composition with a heated gas. In some specific embodiments, a method comprises contacting a composition with a heated gas having a temperature of 190° C. to 250° C. In some embodiments, a method comprises contacting a composition with a heated surface. In some specific embodiments, a method comprises contacting a composition with a heated surface having a temperature of 190° C. to 250° C.

In some embodiments, a method comprises directing a composition comprising cannabinoids along a path having a length of at least 4 meters, in which the composition is contacted with sufficient energy to convert a native cannabinoid molecule of the composition into (i) a carbon dioxide molecule and (ii) a modified cannabinoid molecule in a gas phase while the composition is being directed along the path. Increasing the length of a path increases the probability that a first native cannabinoid molecule will interact with either a second native cannabinoid molecule or other catalyst with an appropriate orientation to catalyze the decarboxylation of the first native cannabinoid molecule.

In some embodiments, a method comprises directing a composition along a path having a length of at least 4 meters at a rate of at least 2 meters per second. Directing a composition along a path of a specific length at a specific rate can control the amount of energy that contacts the composition.

In some embodiments, a path comprises one or more surfaces, and a method comprises heating the one or more surfaces to a temperature of 190° C. to 250° C.

In some embodiments, a composition comprises a non-volatile molecule, and a method comprises separating a modified cannabinoid molecule in a gas phase from the non-volatile molecule. In some specific embodiments, separating a modified cannabinoid molecule in a gas phase from a non-volatile molecule is performed after converting a native cannabinoid molecule into (i) a carbon dioxide molecule and (ii) the modified cannabinoid molecule in the gas phase. In some specific embodiments, separating a modified cannabinoid molecule in a gas phase from a non-volatile molecule is performed prior to contacting the modified cannabinoid molecule with a heat sink. In some very specific embodiments, a method comprises separating a modified cannabinoid molecule in a gas phase from a non-volatile molecule by directing the gas phase through a cyclone. In some very specific embodiments, a method comprises separating a modified cannabinoid molecule in a gas phase from a non-volatile molecule by directing the gas phase through a filter such as an air filter. In some specific embodiments, a method comprises collecting a non-volatile molecule. Non-volatile molecules optionally include one or more of chlorophyll, cellulose, nucleic acids, proteins, carbohydrates, sugars, glycerol, triglyceride, phospholipid, glycerol, fatty acids, salts, ions, ash, glass, sand, rock, metal, and certain microwave-absorbing agents.

In some embodiments, a method converts less than 2% of a cannabinoid molecule of a composition into cannabinol (which is also known as 6,6,9-trimethyl-3-pentyl-benzo[c]chromen-1-ol) by mole. In some very specific embodiments, a method comprises producing a liquid distillate comprising a condensed cannabinoid molecule and cannabinol at a molar ratio greater than 100:1.

In some specific embodiments, a composition comprises CBDA, and a method converts less than 2% of the CBDA of the composition into cannabinol by mole. In some very specific embodiments, a method comprises producing a liquid distillate comprising CBD and cannabinol at a molar ratio greater than 100:1. In some specific embodiments, a composition comprises THCA, and a method converts less than 2% of the THCA of the composition into cannabinol by mole. In some very specific embodiments, a method comprises producing a liquid distillate comprising THC and cannabinol at a molar ratio greater than 100:1.

In some embodiments, a method converts less than 0.2% of a cannabinoid molecule of a composition into 6,6,9-trimethyl-3-pentyl-6a,7,10,10a-tetrahydro-6H-benzo[c]chromen-1-ol ("Δ8-THC" or "delta-8-tetrahydrocannabinol") by mole. In some very specific embodiments, a method comprises producing a liquid distillate comprising a condensed cannabinoid molecule and Δ8-THC at a molar ratio greater than 300:1.

In some specific embodiments, a composition comprises CBDA, and a method converts less than 0.2% of the CBDA of the composition into Δ8-THC by mole. In some very specific embodiments, a method comprises producing a liquid distillate comprising CBD and Δ8-THC at a molar ratio greater than 300:1. In some specific embodiments, a composition comprises THCA, and a method converts less than 0.2% of the THCA of the composition into Δ8-THC by mole. In some very specific embodiments, a method comprises producing a liquid distillate comprising THC and Δ8-THC at a molar ratio greater than 300:1.

In some specific embodiments, a method converts less than 2% of a native cannabinoid molecule of a composition into cannabinol by mole. In some very specific embodiments, a composition comprises a native cannabinoid molecule, the native cannabinoid molecule is CBDA, and a method converts less than 2% of the CBDA into cannabinol by mole. In some very specific embodiments, a composition comprises a native cannabinoid molecule, the native cannabinoid molecule is THCA, and a method converts less than 2% of the THCA into cannabinol by mole.

In some specific embodiments, a method converts less than 0.2% of a native cannabinoid molecule into Δ8-THC by mole. In some very specific embodiments, a composition comprises a native cannabinoid molecule, the native cannabinoid molecule is CBDA, and a method converts less than 0.2% of the CBDA into Δ8-THC by mole. In some very specific embodiments, a composition comprises a native cannabinoid molecule, the native cannabinoid molecule is THCA, and a method converts less than 0.2% of the THCA into Δ8-THC by mole.

In some embodiments, a heat sink has a surface area greater than 10% of the surface area of a composition comprising cannabinoids. A heat sink having a relatively large surface area allows for rapid condensation. In some specific embodiments, a heat sink is a colloid comprising a gas-phase dispersion medium. In some very specific embodiments, a heat sink is an aerosol or a foam. In some very specific embodiments, a heat sink is a spray. Colloids such as aerosols and foams generally have large surface areas, and colloids are therefore suitable heat sinks.

In some embodiments, a heat sink comprises a volatile liquid. Heat sinks comprising a volatile liquid are particularly useful because the vaporization of a volatile liquid can absorb a large amount of energy. In some specific embodiments, a heat sink comprises a volatile liquid, and the volatile liquid comprises one or both of ethanol and water. In some very specific embodiments, a heat sink comprises a volatile liquid, and the volatile liquid comprises ethanol and water at a combined concentration by weight of at least 90%.

In some embodiments, contacting a modified cannabinoid molecule with a heat sink comprises passive cooling such as by exposing the modified cannabinoid molecule or a container comprising the modified cannabinoid molecule to ambient temperature. In some specific embodiments, exposing a modified cannabinoid molecule or a container comprising the modified cannabinoid molecule to ambient temperature comprises cooling in an autoclave. In some specific embodiments, exposing a modified cannabinoid molecule to ambient temperature comprises directing the modified cannabinoid molecule through a fluid-cooled condenser.

In some embodiments, a method comprises contacting a modified cannabinoid molecule with a heat sink less than 240 seconds after contacting a composition with sufficient energy to convert a native cannabinoid molecule into (i) a carbon dioxide molecule and (ii) the modified cannabinoid molecule in a gas phase. In some embodiments, a method comprises condensing a modified cannabinoid molecule into a condensed cannabinoid molecule less than 240 seconds after contacting a composition with sufficient energy to convert a native cannabinoid molecule into (i) a carbon dioxide molecule and (ii) the modified cannabinoid molecule in a gas phase.

In some specific embodiments, a method comprises producing a liquid distillate comprising cannabinol at a concentration less than 0.8% by weight. In some very specific embodiments, a method comprises producing a liquid distillate comprising one or both of CBD and THC at a combined concentration greater than 6% by weight and cannabinol at a concentration less than 0.8% by weight.

In some very specific embodiments, a method comprises producing a liquid distillate comprising cannabinoids, and less than 2% of the cannabinoids of the liquid distillate comprise a carboxyl group. In some very specific embodiments, a method comprises converting at least 95% of a native cannabinoid molecule of a composition into a condensed cannabinoid molecule in a liquid distillate by mole.

In some embodiments, a method comprises producing a liquid distillate comprising condensed cannabinoid molecules selected from one, two, three, four, or each of CBD, CBDV, THC, THCV, and CBG. In some specific embodiments, a method comprises producing a liquid distillate comprising condensed cannabinoid molecules in which at least 95% of the condensed cannabinoid molecules of the liquid distillate are CBD, CBDV, THC, THCV, and CBG by weight.

In some embodiments, a method comprises producing a liquid distillate comprising ethanol. In some specific embodiments, a method comprises producing a liquid distillate comprising ethanol at a concentration of at least 50% by weight. Ethanol reduces the viscosity of a liquid distillate, which improves the flow of a liquid distillate in an automated system.

In some embodiments, a liquid distillate comprises a non-cannabinoid molecule and a condensed cannabinoid molecule, and a method comprises separating the non-cannabinoid molecule from the condensed cannabinoid molecule to produce a product. In some embodiments, a liquid distillate comprises a non-cannabinoid molecule and a condensed cannabinoid molecule, and a method comprises separating the non-cannabinoid molecule from the condensed cannabinoid molecule to produce a product comprising the condensed cannabinoid molecule at a concentration of at least 55% by weight. In some embodiments, a liquid distillate comprises a non-cannabinoid molecule and a condensed cannabinoid molecule, and a method comprises separating the non-cannabinoid molecule from the condensed cannabinoid molecule to produce a product comprising the condensed cannabinoid molecule at a concentration of 55% to 80% by weight. In some embodiments, a liquid distillate comprises a non-cannabinoid molecule and a condensed cannabinoid molecule, and a method comprises separating the non-cannabinoid molecule from the condensed cannabinoid molecule to produce a product comprising the condensed cannabinoid molecule at a concentration of 75% to 99.9% by weight.

In some embodiments, a liquid distillate comprises a non-cannabinoid molecule and CBD, and a method comprises separating the non-cannabinoid molecule from the CBD to produce a product comprising the CBD at a concentration of at least 55% by weight. In some embodiments, a liquid distillate comprises a non-cannabinoid molecule and CBD, and a method comprises separating the non-cannabinoid molecule from the CBD to produce a product comprising the CBD at a concentration of 55% to 80% or 75% to 99.9% by weight.

In some embodiments, a liquid distillate comprises a non-cannabinoid molecule and CBDV, and a method comprises separating the non-cannabinoid molecule from the CBDV to produce a product comprising the CBDV at a concentration of at least 0.7% by weight. In some embodiments, a liquid distillate comprises a non-cannabinoid molecule and CBDV, and a method comprises separating the non-cannabinoid molecule from the CBDV to produce a product comprising the CBDV at a concentration of 0.1% to 10% by weight.

In some embodiments, a liquid distillate comprises a non-cannabinoid molecule and THC, and a method comprises separating the non-cannabinoid molecule from the THC to produce a product comprising the THC at a concentration of at least 55% by weight. In some embodiments, a liquid distillate comprises a non-cannabinoid molecule and THC, and a method comprises separating the non-cannabinoid molecule from the THC to produce a product comprising the THC at a concentration of 55% to 80% or 75% to 99.9% by weight.

In some embodiments, a liquid distillate comprises a non-cannabinoid molecule and THCV, and a method comprises separating the non-cannabinoid molecule from the THCV to produce a product comprising the THCV at a concentration of at least 0.7% by weight. In some embodiments, a liquid distillate comprises a non-cannabinoid molecule and THCV, and a method comprises separating the non-cannabinoid molecule from the THCV to produce a product comprising the THCV at a concentration of 0.1% to 10% by weight.

The following examples provide a framework to implement certain aspects of the disclosure in commercially-viable processes, and these examples do not limit the scope of this patent document or any claim that matures from the disclosure of this patent document.

EXEMPLIFICATION

Example 1. Decarboxylation and Distillation of Cannabinoids from Organic Industrial Hemp Example 1 is prophetic and representative of actual methods. The method of PCT Patent Application Publication No. WO 2016/161420 A1 is performed using organic industrial hemp. The water content of the hemp is less than 10% by weight. The cannabinoid content of the hemp is about 11-12% by weight and consists of about 11% CBDA, 0.1% CBD, 0.3% THCA, and 0% THC by weight (see, for example, FIG. 1). The hemp is ground and sifted to provide a particulate having an average diameter less than 2 mm and a surface-area-to-volume ratio greater than 3000 per meter. The hemp is suspended in heated gas to vaporize the cannabinoids. The heated gas is produced by resistive heating at 10-20 kW. The oxygen content of the heated gas is significantly below the ~20% oxygen content of air by volume. Oxygen is reduced relative to air by blanketing the distillation machine in an inert gas and by evaporating water from the hemp. The heated gas and suspended hemp are directed through heated tubes having a length of 5 to 50 meters at a rate of 5 to 20 meters per second. A known mass of hemp is directed through the heated tubes at a known rate such that the hemp is exposed to less than 100 kJ of energy per gram of the hemp. The heated tubes reverse direction in Cartesian space several times to increase the number of collisions between particles and gas-phase molecules. Cannabinoid vapor is mechanically separated from suspended non-volatile molecules of the hemp using a cyclone and filters. Cannabinoid vapor is condensed approximately 1 to 5 seconds after vaporization. A liquid distillate is collected by rinsing the condensed cannabinoids from the surfaces of the heat sink with ethanol. Greater than 90% of the cannabinoids of the hemp are recovered as cannabinoids of the liquid distillate by mole. Greater than 95% of the cannabinoids of the liquid distillate are decarboxylated. A rotary evaporator is used to remove ethanol and water from the liquid distillate to produce a uniform product comprising at least 10% by weight cannabinoids.

Figure 2:
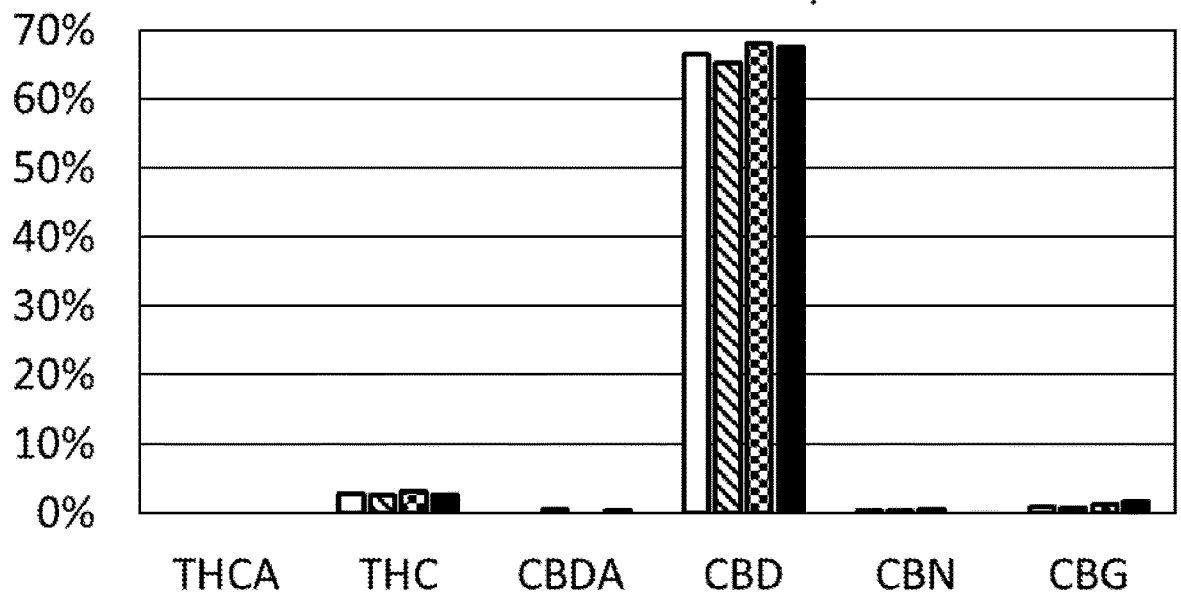
FIG. 2 is a bar graph depicting the THCA, THC, CBDA, CBD, CBN, and CBG concentrations found in four different concentrate products produced according to methods disclosed in this patent document.

Example 2. Products Produced by Decarboxylation and Distillation of Cannabinoids from Organic Industrial Hemp The method of Example 1 was performed on four different batches of organic hemp, and cannabinoid concentrations of concentrated products produced from the liquid distillates were determined by an accredited, third-party cannabis testing laboratory. Actual cannabinoid concentrations by weight of concentrated products produced from liquid distillates are shown in FIG. 2 and Table 1. In each instance, greater than 99.5% of the cannabinoids of the concentrated products were decarboxylated.

TABLE 1

Actual Concentrations of Cannabinoids in Four Concentrated Products Produced from Liquid Distillate Following Decarboxylation and Distillation of the Cannabinoids from Organic Industrial Hemp

|  | 1 | 2 | 3 | 4 |
|---|---|---|---|---|
| CBD | 66.5% | 65.2% | 68.1% | 67.6% |
| CBDA | 0.0% | 0.6% | 0.0% | 0.3% |
| THC | 2.7% | 2.6% | 3.2% | 2.6% |
| THCA | 0.0% | 0.0% | 0.0% | 0.0% |
| CBN | 0.4% | 0.3% | 0.4% | 0.0% |
| CBG | 0.96% | 0.76% | 1.27% | 1.62% |

Example 3. Decarboxylation and Distillation of Cannabinoids from Organic Cannabis Example 3 is prophetic and representative of actual methods. The method of PCT Patent Application Publication No. WO 2016/161420 A1 is performed using organic cannabis. The water content of the cannabis is less than 10% by weight. The cannabinoid content of the cannabis is about 20-30% by weight. The cannabis is ground and sifted to provide a particulate having an average diameter less than 2 mm and a surface-area-to-volume ratio greater than 3000 per meter. The cannabis is suspended in heated gas to vaporize the cannabinoids. The heated gas is produced by resistive heating at 10-20 kW. The oxygen content of the heated gas is significantly below the ~20% oxygen content of air by volume. Oxygen is reduced relative to air by blanketing the distillation machine in an inert gas and by evaporating water from the cannabis. The heated gas and suspended cannabis are directed through heated tubes having a length of 5 to 50 meters at a rate of 5 to 20 meters per second. A known mass of cannabis is directed through the heated tubes at a known rate such that the cannabis is exposed to less than 100 kJ of energy per gram of the cannabis. The heated tubes reverse direction in Cartesian space several times to increase the number of collisions between particles and gas-phase molecules. Cannabinoid vapor is mechanically separated from suspended non-volatile molecules of the cannabis using a cyclone and filters. Cannabinoid vapor is condensed approximately 1 to 5 seconds after vaporization. A liquid distillate is collected by rinsing the condensed cannabinoids from the surfaces of the heat sink with ethanol. Greater than 90% of the cannabinoids of the cannabis are recovered as cannabinoids of the liquid distillate by mole. Greater than 95% of the cannabinoids of the liquid distillate are decarboxylated. A rotary evaporator is used to remove ethanol and water from the liquid distillate to produce a uniform product comprising at least 10% by weight cannabinoids.

What is claimed is:

1. A method to chemically-modify a cannabinoid molecule, comprising:
providing a composition comprising cannabinoids, wherein the composition has a surface-area-to-volume ratio that is greater than 1000 per meter; the cannabinoids comprise a native cannabinoid molecule; the native cannabinoid molecule comprises a carboxyl group; and the native cannabinoid molecule is in either a liquid phase or a solid phase;
contacting the composition with sufficient energy to convert the native cannabinoid molecule into (i) a carbon dioxide molecule and (ii) a modified cannabinoid molecule in a gas phase;
contacting the modified cannabinoid molecule with a heat sink to condense the modified cannabinoid molecule into a condensed cannabinoid molecule in a liquid distillate; and
collecting the liquid distillate.

2. The method of claim 1, wherein:
the composition comprises a particle;
the particle comprises the native cannabinoid molecule;
the method comprises suspending the particle in the gas phase; and
the method comprises contacting the composition with the sufficient energy while the particle is suspended in the gas phase.

3. The method of claim 1, wherein:
the composition comprises a droplet;
the droplet comprises the native cannabinoid molecule;
the method comprises suspending the droplet in the gas phase; and
the method comprises contacting the composition with the sufficient energy while the droplet is suspended in the gas phase.

4. The method of claim 1, wherein contacting the composition with the sufficient energy comprises contacting the composition with less than 100 kilojoules of energy per gram of the composition.

5. The method of claim 1, wherein contacting the composition with the sufficient energy comprises contacting the composition with at least 1 kilowatt of power and no greater than 100 kilowatts of power for at least 200 milliseconds and no greater than 20 seconds.

6. The method of claim 1, wherein contacting the composition with the sufficient energy comprises irradiating the composition.

7. The method of claim 1, wherein contacting the composition with the sufficient energy comprises convectively heating the composition.

8. The method of claim 1, wherein contacting the composition with the sufficient energy comprises conductively heating the composition.

9. The method of claim 1, comprising directing the composition along a path having a length of at least 4 meters at a rate of at least 2 meters per second.

10. The method of claim 9, wherein the path comprises one or more surfaces, and the method comprises heating the one or more surfaces to a temperature of at least 190 degrees Celsius and no greater than 250 degrees Celsius.

11. The method of claim 1, wherein:
the composition comprises a non-volatile molecule;
the method comprises separating the modified cannabinoid molecule from the non-volatile molecule;
the separating is performed after converting the native cannabinoid molecule into (i) the carbon dioxide molecule and (ii) the modified cannabinoid molecule in the gas phase; and
the separating is performed prior to contacting the modified cannabinoid molecule with the heat sink.

12. The method of claim 11, wherein the non-volatile molecule is either chlorophyll, cellulose, a nucleic acid, a protein, a carbohydrate, a sugar, a triglyceride, or a phospholipid.

13. The method of claim 1, comprising contacting the modified cannabinoid molecule with the heat sink less than 240 seconds after contacting the composition with the sufficient energy.

14. The method of claim 1, wherein:
the liquid distillate comprises one or both of cannabidiol and tetrahydrocannabinol at a combined concentration of greater than 6 percent by weight; and
the liquid distillate comprises cannabinol at a concentration of less than 0.8 percent by weight.

15. The method of claim 1, wherein the liquid distillate comprises each of cannabidiol, tetrahydrocannabinol, and cannabigerol.

16. The method of claim 1, wherein the liquid distillate comprises ethanol at a concentration of at least 50 percent by weight.

17. The method of claim 1, wherein:
the liquid distillate comprises a non-cannabinoid molecule and the condensed cannabinoid molecule; and
the method comprises separating the non-cannabinoid molecule from the condensed cannabinoid molecule to produce a product comprising the condensed cannabinoid molecule at a concentration of at least 55 percent by weight.

18. The method of claim 1, wherein:
the native cannabinoid molecule is cannabigerolic acid;
the modified cannabinoid molecule is cannabigerol; and
the condensed cannabinoid molecule is cannabigerol.

19. A method to chemically-modify a cannabinoid molecule, comprising:
providing a composition comprising cannabinoids, wherein the composition has a surface-area-to-volume ratio that is greater than 1000 per meter; the cannabinoids comprise a native cannabinoid molecule; the native cannabinoid molecule comprises a carboxyl group; the native cannabinoid molecule is in either a liquid phase or a solid phase; the composition comprises a particle; the particle comprises the native cannabinoid molecule; and the composition comprises a non-volatile molecule;
suspending the particle in a gas phase;
contacting the composition with sufficient energy to convert the native cannabinoid molecule into (i) a carbon dioxide molecule and (ii) a modified cannabinoid molecule in the gas phase while the particle is suspended in the gas phase, wherein the sufficient energy is less than 100 kilojoules of energy per gram of the composition;
separating the modified cannabinoid molecule from the non-volatile molecule;
contacting the modified cannabinoid molecule with a heat sink to condense the modified cannabinoid molecule into a condensed cannabinoid molecule in a liquid distillate;
collecting the liquid distillate, wherein the liquid distillate comprises the condensed cannabinoid molecule and a non-cannabinoid molecule; and
separating the non-cannabinoid molecule from the condensed cannabinoid molecule to produce a product comprising the condensed cannabinoid molecule at a concentration of at least 55 percent by weight.

20. A method to chemically-modify a cannabinoid molecule, comprising:
providing a composition comprising cannabinoids, wherein the composition has a surface-area-to-volume ratio that is greater than 1000 per meter; the cannabinoids comprise a native cannabinoid molecule; the native cannabinoid molecule comprises a carboxyl group; the native cannabinoid molecule is cannabigerolic acid; the native cannabinoid molecule is in either a liquid phase or a solid phase; the composition comprises a particle; the particle comprises the native cannabinoid molecule; and the composition comprises a non-volatile molecule;
suspending the particle in a gas phase;
contacting the composition with sufficient energy to convert the native cannabinoid molecule into (i) a carbon dioxide molecule and (ii) a modified cannabinoid molecule in the gas phase while the particle is suspended in the gas phase, wherein the sufficient energy is less than 100 kilojoules of energy per gram of the composition, and the modified cannabinoid molecule is cannabigerol;
separating the modified cannabinoid molecule from the non-volatile molecule;
contacting the modified cannabinoid molecule with a heat sink to condense the modified cannabinoid molecule into a condensed cannabinoid molecule in a liquid distillate, wherein the condensed cannabinoid molecule is cannabigerol;
collecting the liquid distillate, wherein the liquid distillate comprises the condensed cannabinoid molecule and a non-cannabinoid molecule; and
separating the non-cannabinoid molecule from the condensed cannabinoid molecule to produce a product comprising the condensed cannabinoid molecule at a concentration of at least 55 percent by weight.

* * * * *